United States Patent [19]

Stanton et al.

[11] Patent Number: 4,678,800
[45] Date of Patent: Jul. 7, 1987

[54] GAMMA-R-GLUTAMOYL DERIVATIVES

[75] Inventors: James L. Stanton, Ossining; Gary M. Ksander, Carmel, both of N.Y.

[73] Assignee: Ciba-Geigy Corporation, Ardsley, N.Y.

[21] Appl. No.: 621,302

[22] Filed: Jun. 15, 1984

[51] Int. Cl.$^4$ .................. C07D 209/12; A61K 31/40
[52] U.S. Cl. ..................... 514/412; 514/333; 514/339; 514/419; 546/147; 546/256; 546/273; 548/201; 548/452; 548/491; 548/533; 562/450; 562/503
[58] Field of Search ............... 548/491, 452; 514/419, 514/333, 339, 412; 546/256, 273, 256

[56] References Cited

U.S. PATENT DOCUMENTS

| | | | |
|---|---|---|---|
| 3,331,828 | 7/1967 | Inamine et al. | 260/112.5 |
| 4,052,511 | 10/1977 | Cushman et al. | 424/274 |
| 4,311,705 | 1/1982 | Ondetti et al. | 424/274 |
| 4,329,473 | 5/1982 | Almquist et al. | 548/433 X |
| 4,374,847 | 2/1983 | Gruenfeld | 548/430 X |
| 4,396,773 | 8/1983 | Kim et al. | 548/491 |
| 4,404,206 | 9/1983 | Vincent et al. | 546/5 X |
| 4,405,787 | 9/1983 | Gaitanopoulos | 546/112 |
| 4,568,489 | 2/1986 | Floyd | 548/491 X |
| 4,587,258 | 5/1986 | Gold et al. | 514/412 |

OTHER PUBLICATIONS

International Application WO83/03828, Published Nov. 10, 1983, 76 pages.
M. Ondetti et al; Peptides-Proc. Fifth Am. Pept. Symposium; 1977; pp. 576-578.
S. Magnan et al; J. Med. Chem.; 25, (1982); pp. 1018-1021.
T. Kasai et al; Acta Chemica Scand.; B 33, (1979); pp. 213-218.
M. Lieflander et al; Z. Physiol. Chem., 320, (1960), pp. 35-57.
N. Tal et al; J. Neurochem.; 1982, pp. 574-576.
N. Gruenfeld et al.; J. Med. Chem.; 26, (1983), pp. 1277-1282.

Primary Examiner—Joseph Paul Brust
Attorney, Agent, or Firm—Norbert Gruenfeld

[57] ABSTRACT

A compound of the formula

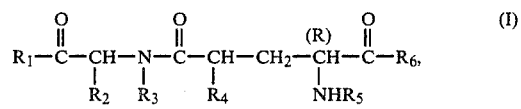

wherein $R_1$ and $R_6$ independently represent hydroxy, $C_1$-$C_4$-alkoxy, substituted $C_1$-$C_4$-alkoxy, amino, or substituted amino, $R_2$ represents hydrogen, $C_1$-$C_4$-alkyl, or $C_2$-$C_4$-alkenyl, $R_3$ represents cyclo-$C_3$-$C_6$-alkyl, phenyl, phenyl substituted by $C_1$-$C_4$-alkyl, halogen, nitro, or $C_1$-$C_4$-alkoxy, or cyclo-$C_3$-$C_6$-alkyl fused with benzene, or wherein $R_2$ and $R_3$ are connected and together with the adjacent —CH-group and the adjacent N-atom form a saturated or partially saturated, monocyclic, five- or six-membered heterocyclic group or form a saturated or partially saturated, bicyclic heterocyclic group containing five or six atoms per ring, $R_4$ represents hydrogen or $C_1$-$C_4$-alkyl, and $R_5$ represents an acyl group, are useful as antihypertensive and cardioactive agents. The invention also relates to processes for preparing the compounds of the formula I and to pharmaceutical compositions.

11 Claims, No Drawings

GAMMA-R-GLUTAMOYL DERIVATIVES

The invention relates to novel compounds of the formula I which are useful as antihypertensive and/or cardioactive agents, to pharmaceutical compositions that contain the compounds of the formula I, to the use of these compounds as medicaments, for example in a method for treating cardiovascular diseases such as hypertension or congestive heart failure by administering an effective amount of said compounds to mammals including man, and to processes for the preparation of compounds of the formula I.

Particularly, the invention relates to a compound of the formula:

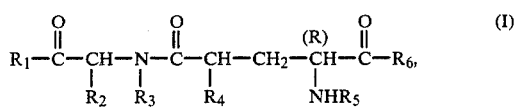

wherein $R_1$ and $R_6$ independently represent hydroxy, $C_1$–$C_4$-alkoxy, substituted $C_1$–$C_4$-alkoxy, amino, or substituted amino, $R_2$ represents hydrogen, $C_1$–$C_4$-alkyl, or $C_2$–$C_4$-alkenyl, $R_3$ represents cyclo-$C_3$–$C_6$-alkyl, phenyl, phenyl substituted by $C_1$–$C_4$-alkyl, halogen, nitro, or $C_1$–$C_4$-alkoxy, or cyclo-$C_3$–$C_6$-alkyl fused with benzene, or wherein $R_2$ and $R_3$ are connected and together with the adjacent —CH-group and the adjacent N-atom form a saturated or partially saturated, monocyclic, five- or six-membered heterocyclic group or form a saturated or partially saturated, bicyclic heterocyclic group containing five or six atoms per ring, $R_4$ represents hydrogen or $C_1$–$C_4$-alkyl, and $R_5$ represents an acyl group, to a salt of a compound that contains a salt forming group, to stereoisomers, mixtures of these stereoisomers, to a pharmaceutical composition that contains this compound or its pharmaceutically acceptable salt, to the use of this compound as medicament and to processes for the preparation of a compound of the formula I.

In the specification of the present invention, the term "lower" whenever used for the definition of groups or radicals, for example lower alkyl, lower alkylene, lower alkoxy, lower alkanoyl etc., means that,unless expressly stated otherwise, the groups or radicals defined by this term contain up to 7, and preferably up to 4 carbon atoms inclusively.

If $R_2$ is other than hydrogen and $R_4$ is hydrogen, compounds of the formula I may be (R,S), (R)-diastereomers, (R),(R)-enantiomers or, preferably, (S),(R)-enantiomers.

If $R_2$ is other than hydrogen and $R_4$ is $C_1$–$C_4$-alkyl, compounds of the formula I are preferably (S),(R),(R)-enantiomers.

The generic terms used in the specification of this invention preferably are defined as follows:

$C_1$–$C_4$-alkoxy $R_1$ or $R_6$ is for example, tert-butoxy, isobutoxy, n-butoxy, n-propoxy, isopropoxy, or, preferably, methoxy or ethoxy.

Substituted alkoxy $R_1$ or $R_6$ is for example, methoxy, ethoxy or n-propoxy substituted by carbocyclic aryl, for example phenyl, heterocyclic aryl, for example 2-, 3- or 4-pyridyl, amino, $C_1$–$C_4$-alkylamino, for example methylamino, or di-$C_1$–$C_4$-alkylamino, for example dimethylamino.

Substituted alkoxy $R_1$ or $R_6$ is preferably acyloxy-$C_1$–$C_3$-alkoxy that can be cleaved under physiological conditions, wherein acyl represents, for example, the acyl group of a carboxylic acid, a carbonic acid monoester or of an amino acid, or wherein acyloxy forms the radical of a lactone.

Acyl is preferably the acyl group of a straight chain or a branched lower alkanecarboxylic acid, the acyl group of a branched carbonic acid that is monoesterified by optionally branched lower alkyl, or the acyl group of a straight chain or a branched α-amino-lower alkanecarboxylic acid.

Acyloxy-$C_1$–$C_3$-alkoxy that can be cleaved under physiological conditions is preferably lower alkanoyloxylower alkoxy, for example lower alkanoyloxymethoxy or lower alkanoyloxyethoxy, for example acetoxymethoxy, pivaloyloxymethoxy or 1-propionyloxyethoxy, lower alkoxycarbonyloxylower alkoxy, for example 1-ethoxycarbonyloxyethoxy or tert-butoxycarbonyloxymethoxy, amino-lower alkanoyloxymethoxy, especially α-amino-lower alkanoyloxymethoxy, for example glycyloxymethoxy, S-valyloxymethoxy, or S-leucyloxymethoxy.

Substituted amino $R_1$ or $R_6$ is, for example mono- or di-$C_1$–$C_4$-alkylamino, for example, dimethyl- or diethylamino or a five- or six membered saturated heterocyclyl moiety which has at least one carbon atom, 1–3 nitrogen atoms and optionally a sulfur or oxygen atom and which can be substituted by hydroxy, $C_1$–$C_4$-alkyl, for example methyl, or hydroxy-$C_2$–$C_4$-alkyl, for example 2-hydroxyethyl, and which is bonded with a nitrogen atom to the adjacent carbonyl group, for example pyrrolidin-1-yl, piperid-1-yl, 4-(2-hydroxyethyl)-piperazin-1-yl, or morpholin-1-yl.

Substituted amino $R_1$ or $R_6$ is also an amino acid group preferably derived from an amino acid which is present in proteins, especially glycine (H—Gly—OH), alanine (H—Ala—OH), serine (S—Ser—OH), cysteine (H—Cys—OH), tyrosine (H—Tyr—OH), asparagine (H—Asn—OH), glutamine (H—Gln—OH), aspartic acid (H—Asp—OH), glutamic acid (H—Glu—OH), arginine (H—Arg—OH), histidine (H—His—OH), including those 8 amino acids which are essential for man, for example valine (H—Val—OH), leucine (H—Leu—OH), isoleucine (H—Ile—OH), lysine (H—Lys—OH), phenylalanine (H—Phe—OH), tryptophane (H—Trp—OH), methionine (H—Met—OH), and threonine (H—Thr—OH) and which is connected at the amino group of these amino acids with the group

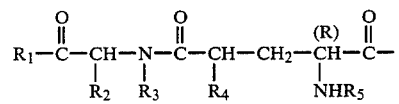

The carboxy group of these amino acids can be amidated or esterified, for example by $C_1$–$C_4$-alkyl, for example methyl, ethyl or tert-butyl.

$C_1$–$C_4$-alkyl $R_2$ or $R_4$ is, for example, ethyl, n-propyl, isopropyl, n-butyl or, preferably, methyl.

$C_2$–$C_4$-alkenyl $R_2$ is, for example, vinyl or allyl.

Cyclo-$C_3$–$C_6$-alkyl $R_3$ is, for example, cyclopropyl, cyclobutyl or, preferably, cyclopentyl or cyclohexyl.

Phenyl substituted by $C_1$–$C_4$-alkyl, halogen, nitro, or $C_1$–$C_4$-alkoxy $R_3$ is, for example, 2-, 3- or 4-methylphenyl, 2-, 3- or 4-chlorophenyl, 2,3-dichlorophenyl, 2-, 3- or 4-nitrophenyl, or, preferably, 2-, 3- or 4-methoxyphenyl or 3,4-dimethoxyphenyl.

Cyclo-$C_4$–$C_6$-alkyl fused with benzene $R_3$ is, for example, indan-1-yl or tetrahydronaphth-1-yl.

A saturated or partially saturated, monocyclic, five or six-membered heterocyclic group or a saturated or partially saturated, bicyclic heterocyclic group containing five or six atoms per ring is formed by the group

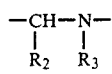

and is aza-, diaza-, triaza-, thiaza-, thiadiaza-, oxaza-, or oxadiazacyclyl which is substituted at the carbon adjacent to the nitrogen by the group

and at the nitrogen by the group

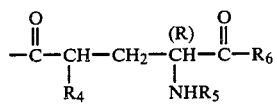

Further substituents of this heterocyclic group are, for example, hydroxy, $C_1$–$C_4$-alkyl, for example methyl, $C_1$–$C_4$-alkoxy, for example methoxy, phenyl, hydroxyphenyl, for example 2-, 3- or 4-hydroxyphenyl, cyclo-$C_3$–$C_6$-alkyl, for example cyclopropyl, cyclopentyl or cyclohexyl, or a cyclo-$C_3$–$C_6$-alkylidene moiety, for example cyclopropylidene, cyclopentylidene, or cyclohexylidene.

Saturated or partially saturated, monocyclic, five- or six-membered aza-, diaza-, triaza-, thiaza-, thiadiaza-, oxaza- or oxadiazacyclyl is, for example, pyrrolidinyl, pyrrolinyl, imidazolidinyl, imidazolinyl, piperidinyl, piperazinyl, morpholinyl, or thiazolidinyl.

Saturated bicyclic, aza-, diaza-, triaza-, thiaza-, thiadiaza-, oxaza- or oxadiazacyclyl containing five or six atoms per ring is for example, 2- or 7-azabicyclo[2.2.1]heptyl, 2-azabicyclo[2.2.2]octyl, 2-, 3-, 6- or 8-azabicyclo[3.2.1]octyl, 2-azabicyclo[3.3.0]octyl, 2,6-diazabicyclo[2.2.2]octyl, 3,7-diazabicyclo[3.3.1]nonyl, or 2-oxa-5-azabicyclo[2.2.1]heptyl, or, preferably, decahydroquinolyl, decahydroisoquinolyl, or octahydroindolyl.

Partially saturated, bicyclic, aza-, diaza-, triaza-, thiaza-, thiadiaza-, oxaza-, or oxadiazacyclyl containing five or six atoms per ring is for example tetrahydroquinolyl, tetrahydroisoquinolyl, dihydroindolyl, tetrahydroimidazole[2,3-c]pyridyl, tetrahydrothieno[2,3-c]pyridyl, tetrahydrothieno[3,2-c]pyridyl, or tetrahydrothieno[3,4-c]pyridyl.

These heterocyclic groups can be substituted, for example, by hydroxy, $C_1$–$C_4$-alkoxy, for example methoxy, or $C_1$–$C_4$-alkyl, for example methyl.

Acyl $R_5$ is, for example, carbamoyl, mono- or di-$C_1$–$C_4$-alkylcarbamoyl, arylcarbamoyl, the acyl group of a carboxylic acid or of a carbonic acid hemiester, sulfo, the acyl group of a sulfonic acid, sulfamoyl, or mono- or di-$C_1$–$C_4$-alkylsulfamoyl.

Mono-$C_1$–$C_4$-alkylcarbamoyl $R_5$ is, for example, methyl- or ethylcarbamoyl.

Di-$C_1$–$C_4$-alkyl carbamoyl $R_5$ is, for example, dimethyl- or diethylcarbamoyl.

Arylcarbamoyl $R_5$ is, for example, phenylcarbamoyl.

The acyl group of a carboxylic acid $R_5$ is, for example, $C_1$–$C_4$-alkanoyl, for example formyl, acetyl, propionyl, or pivaloyl, aryl-$C_1$–$C_4$-alkanoyl, for example, benzoyl, phenylacetyl or 3-phenyl-n-propionyl, or heterocyclylcarbonyl, wherein heterocyclyl has at least one C-atom and 1–3 nitrogen atoms and optionally one oxygen or sulfur atom as ring members, and wherein heterocyclyl can be substituted by $C_1$–$C_4$-alkyl, for example methyl and/or oxo, for example pyrrolidin-2-ylcarbonyl, piperidin-2-ylcarbonyl, 1-($C_1$–$C_4$-alkyl)-piperidin-2- or -3-yl, for example 1-methylpiperidin-2-yl, morpholin-2- or -3-yl, or, preferably nicotinoyl, isonicotinoyl or picolinoyl.

The acyl group of a carbonic acid semiester $R_5$ is, for example, $C_1$–$C_4$-alkoxycarbonyl, for example methoxy-, ethoxy- or tert-butoxycarbonyl (BOC), or, preferably, aryl-$C_1$–$C_4$-alkoxycarbonyl, for example benzyloxycarbonyl(cbz).

The acyl group of a sulfonic acid $R_5$ is, for example, $C_1$–$C_4$-alkylsulfonyl, for example mesyl, or arylsulfonyl, for example benzenesulfonyl or p-toluenesulfonyl (pTS).

Mono-$C_1$–$C_4$-alkylsulfamoyl $R_5$ is, for example, methyl- or ethylsulfamoyl.

Di-$C_1$–$C_4$-alkylsulfamoyl $R_5$ is, for example, dimethyl- or diethylsulfamoyl.

Salts of compounds of the formula I are especially pharmaceutically acceptable salts, for example metal or ammonium salts of acids of formula I, wherein $R_1$ and/or $R_6$ represent hydroxy, more particularly alkali or alkaline earth metal salts, for example, the sodium, potassium, magnesium or calcium salt; or ammonium salts formed with ammonia or organic amines, such as mono-, di- or tri-lower (alkyl or hydroxyalkyl)-amines, such as methylamine, dimethylamine, diethylamine, diethanolamine, triethanolamine, ethylamine, tris(hydroxymethyl)aminomethane and the like; mono- or di-(cycloalkyl) amines, such as cyclohexylamine and dicyclohexylamine; lower alkylenediamines, such as ethylenediamine; heterocyclic amines, such as morpholine; aryl-lower alkylamines, such as benzylamine and phenethylamine; and quaternary ammonium derivatives thereof, such as benzyl-trimethylammonium hydroxide.

In addition, the compounds of the formula I in which there is a basic group, for example, compounds wherein $R_1$ or $R_6$ is $C_1$–$C_4$-alkyl substituted by amino, $C_1$–$C_4$-alkylamino or di-$C_1$–$C_4$-alkylamino, form salts, particularly pharmaceutically acceptable salts with acids. Any conventional acid can be utilized to form a salt in accordance with this invention.

Compounds of the formula I having an acidic, for example a free carboxy group and a basic group, may also exist in the form of an internal salt, i.e. in the zwitterion form, or one part of the molecule may be in the form of an internal salt and another may be in the form of a normal salt.

For isolation or purification purposes, salts may be obtained which might not be useful for pharmaceutical purposes. However, only pharmaceutically acceptable salts are used for therapeutic purposes and these salts, therefore, are preferred.

In an alphabetically increasing order of preference, the invention relates to the following compounds of the formula I:

(a) A compound of the formula I, wherein $R_1$ represents hydroxy, $C_1$–$C_4$-alkoxy, for example methoxy or ethoxy, di-$C_1$–$C_4$-alkylamino-$C_2$–$C_4$-alkoxy, for example 2-dimethylaminoethoxy or 3-dimethylamino-n- propoxy, heterocyclic aryl-$C_1$-$C_4$-alkoxy, for example pyrid-2-, -3- or -4-yl-methoxy, or amino, $R_3$ represents cyclo-$C_4$-$C_6$-alkyl, for example cyclopentyl or cyclohexyl, phenyl, phenyl substituted by $C_1$-$C_4$-alkoxy, for example 2-, 3-, or 4-methoxyphenyl or 3,4-dimethoxyphenyl, or cyclo-$C_3$-$C_6$-alkyl fused with benzene, for example indan-1- or -2-yl or tetrahydronaphth-1-, -2- or -3-yl, or wherein $R_2$ and $R_3$ are connected and together with the adjacent -CH-group and the adjacent N-atom form a pyrrolidinyl, pyrrolinyl, imidazolidinyl, imidazolinyl, piperidinyl, piperazinyl, morpholinyl or thiazolidinyl moiety which is optionally substituted by phenyl, hydroxyphenyl, for example 2-, 3- or 4-hydroxyphenyl or a cyclo-$C_3$-$C_6$- alkylidene moiety, for example cyclopentylidene or cyclohexylidene, or form a 2- or 7-azabicyclo[2.2.1]heptyl, 2-azabicyclo[2.2.2]octyl, 2-, 3-, 6- or 8-azabicyclo[3.2.1]octyl, 2-azabicyclo[3.3.0]-octyl, decahydroquinolyl, decahydroisoquinolyl, octahydroindolyl, tetrahydroquinolyl, tetrahydroisoquinolyl, or a dihydroindolyl moiety which is optionally substituted by $C_1$-$C_4$-alkoxy, for example methoxy, $R_4$ represents hydrogen, $R_5$ is carbamoyl, $C_1$-$C_4$-alkanoyl, for example acetyl, aryl-$C_1$-$C_4$-alkanoyl, for example benzoyl or phenylacetyl, heterocyclylcarbonyl, for example nicotinoyl, isonicotinoyl or picolinoyl, $C_1$-$C_4$-alkoxycarbonyl, for example tert-butoxycarbonyl (BOC), aryl-$C_1$-$C_4$-alkoxycarbonyl, for example benzyloxycarbonyl (Cbz), $C_1$-$C_4$-alkylsulfonyl, for example mesyl, or arylsulfonyl, for example benzenesulfonyl or p-toluenesulfonyl, and $R_6$ represents hydroxy, $C_1$-$C_4$-alkoxy, for example methoxy or ethoxy, di-$C_1$-$C_4$-alkylamino-$C_2$-$C_4$-alkoxy, for example 2-dimethylaminoethoxy or 3-dimethylamino-n-propoxy, or heterocyclic aryl-$C_1$-$C_4$-alkoxy, for example pyrid-2-, -3- or -4-ylmethoxy and a pharmaceutically acceptable salt of a compound of the formula I that has a salt forming group;

(b) A compound of the formula I, wherein $R_1$ represents hydroxy, $C_1$-$C_4$-alkoxy, for example methoxy or ethoxy, di-$C_1$-$C_4$-alkylamino-$C_2$-$C_4$-alkoxy, for example 2-dimethylaminoethoxy or 3-dimethylamino-n-propoxy, heterocyclic aryl-$C_1$-$C_4$-alkoxy, for example pyrid-2-, -3- or -4-ylmethoxy, or amino, $R_2$ and $R_3$ are connected and together with the adjacent —CH— group and the adjacent N-atom form a pyrrolidinyl, pyrrolinyl, imidazolidinyl, imidazolinyl, piperidinyl, piperazinyl, morpholinyl or thiazolidinyl moiety which is optionally substituted by phenyl, hydroxyphenyl, for example 2-, 3- or 4-hydroxyphenyl or a cyclo-$C_3$-$C_6$- alkylidene moiety, for example cyclopentylidene or cyclohexylidene, or form a 2- or 7-azabicyclo[2.2.1]heptyl, 2-azabicyclo[2.2.2]octyl, 2-, 3-, 6- or 8-azabicyclo[3.2.1]octyl, 2-azabicyclo [3.3.0]octyl, decahydroquinolyl, decahydroisoquinolyl, octahydroindolyl, tetrahydroquinolyl, tetrahydroisoquinolyl, or a dihydroindolyl moiety which is optionally substituted by $C_1$-$C_4$-alkoxy, for example methoxy, $R_4$ represents hydrogen, $R_5$ is $C_1$-$C_4$-alkanoyl, for example acetyl, aryl-$C_1$-$C_4$-alkanoyl, for example benzoyl or phenylacetyl, heterocyclylcarbonyl, for example nicotinoyl, isonicotinoyl or picolinoyl, benzyloxycarbonyl, $C_1$-$C_4$-alkylsulfonyl, for example mesyl, or arylsulfonyl, for example benzenesulfonyl or p-toluenesulfonyl, and $R_6$ represents hydroxy or $C_1$-$C_4$-alkoxy, for example methoxy or ethoxy and pharmaceutically acceptable salt of a compound of the formula I that has a salt forming group;

(c) A compound of the formula I, wherein $R_1$ represents hydroxy, $C_1$-$C_4$-alkoxy, for example methoxy or ethoxy, di-$C_1$-$C_4$-alkylamino-$C_2$-$C_4$-alkoxy, for example 2-dimethylaminoethoxy or 3-dimethylamino-n-propoxy, heterocyclic aryl-$C_1$-$C_4$-alkoxy, for example pyrid-2-, -3-or -4-ylmethoxy, or amino, $R_2$ and $R_3$ are connected and together with the adjacent —CH— group and the adjacent N-atom form a 2-azabicyclo[3.3.0]octyl, decahydroquinolyl, decahydroisoquinolyl, octahydroindolyl, tetrahydroquinolyl, tetrahydroisoquinolyl or dihydroindolyl moiety, $R_4$ represents hydrogen, $R_5$ represents $C_1$-$C_4$-alkanoyl, for example acetyl, aryl-$C_1$-$C_4$-aklanoyl, for example benzoyl or phenylacetyl, heterocyclylcarbonyl, for example nicotinoyl, isonicotinoyl or picolinoyl, benzyloxycarbonyl, $C_1$-$C_4$-alkylsulfonyl, for example mesyl, or arylsulfonyl, for example benzenesulfonyl or p-toluenesulfonyl, and $R_6$ represents hydroxy or $C_1$-$C_4$-alkoxy, for example methoxy or ethoxy, and a pharmaceutically acceptable salt of a compound of the formula I that has a salt forming group;

(d) A compound of the formula I, wherein $R_1$ represents hydroxy, $C_1$-$C_4$-alkoxy, for example methoxy or ethoxy, di-$C_1$-$C_4$-alkylamino-$C_2$-$C_4$-alkoxy, for example 2-dimethylaminoethoxy or 3-dimethylamino-n-propoxy, heterocyclic aryl-$C_1$-$C_4$-alkoxy, for example pyrid-2-, -3- or -4-ylmethoxy, or amino, $R_2$ and $R_3$ are connected and together with the adjacent —CH— group and the adjacent N-atom form a decahydroquinolyl, octahydroindolyl, tetrahydroquinolyl, or dihydroindolyl moiety, $R_4$ represents hydrogen, $R_5$ represents $C_1$-$C_4$-alkanoyl, for example acetyl, aryl-$C_1$-$C_4$-alkanoyl, for example benzoyl or phenylacetyl, heterocyclylcarbonyl, for example nicotinoyl, isonicotinoyl or picolinoyl, benzyloxycarbonyl, $C_1$-$C_4$-alkylsulfonyl, for example mesyl, or arylsulfonyl, for example benzenesulfonyl or p-toluenesulfonyl, and $R_6$ represents hydroxy or $C_1$-$C_4$-alkoxy, for example methoxy or ethoxy, and a pharmaceutically acceptable salt of a compound of the formula I that has a salt forming group;

(e) A compound of the formula

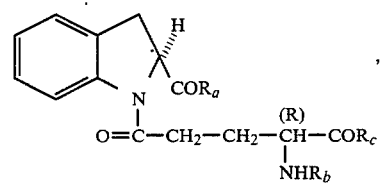

(Ia)

wherein $R_a$ represents hydroxy, $C_1$-$C_4$-alkoxy, for example methoxy or ethoxy, di-$C_1$-$C_4$-alkylamino-$C_2$-$C_4$-alkoxy, for example 2-dimethylaminoethoxy or 3-dimethylamino-n-propoxy, heterocyclic aryl-$C_1$-$C_4$-alkoxy, for example pyrid-2-, -3- or -4-ylmethoxy, or amino, $R_b$ represents $C_1$-$C_4$-alkanoyl, for example acetyl, aryl-$C_1$-$C_4$-alkanoyl, for example benzoyl or phenylacetyl, heterocyclylcarbonyl, for example nicotinoyl, isonicotinoyl or picolinoyl, benzyloxycarbonyl, $C_1$-$C_4$-alkylsulfonyl, for example mesyl, or arylsulfonyl, for example benzenesulfonyl or p-toluenesulfonyl, and $R_c$ represents hydroxy or $C_1$-$C_4$-alkoxy, for example methoxy or ethoxy, and a pharmaceutically acceptable salt of a compound of the formula Ia that has a salt forming group;

The compounds of this invention exhibit valuable pharmacological properties, primarily hypotensive and cardioactive effects, inter alia due to their angiotensin converting enzyme (ACE) inhibitory activity. This is demonstrable by in vivo or in vitro animal tests, using advantageously mammals, e.g., rats, cats, dogs or isolated organs thereof, as test objects. The animals may either be normotensive or hypertensive e.g., genetically hypertensive rats, or renal hypertensive rats and dogs, and sodium-depleted dogs. Said compounds can be applied to them enterally or parenterally, advantageously orally or intravenously, for example within gelatin capsules or in the form of starch suspensions or aqueous solutions, respectively. The applied dosage may range between about 0.01 and 50 mg/kg/day, preferably between about 0.1 and 25 mg/kg/day, advantageously between about 0.1 and 10 mg/kg/day.

The in vivo lowering effect on the blood pressure is recorded either directly by means of a catheter, for example placed in the dog's femoral artery, or indirectly by sphygmomanometry at the rat's tail, and a transducer, expressing the blood pressure prior and after dosing in mm Hg. Thus, for example, the representative members of the compounds of this invention, illustrated by the examples herein, are effective in hypertensive rats and at p.o. doses as low or lower than 10 mg/kg/day. Illustrative of the invention, the two representative test compounds 1-(N-benzyloxycarbonyl-$\gamma$-R-glutamyl)-indoline-2S-carboxylic acid and 1-(N-nicotinoyl-$\gamma$-R-glutamyl)-indoline-2S-carboxylic acid lower blood pressure and decrease the heart rate in the spontaneous hypertensive rat at a dose of 10 mg/kg p.o. or lower.

The compounds of formula I of the invention also exhibit an inhibitory effect against the angiotensin I pressure response of normotensive rats. The enzyme renin, normally causes specific hydrolysis of the circulating protein renin-substrate. This hydrolysis generates angiotensin I, which is further hydrolyzed by the action of said converting enzyme to the potent vasoconstrictor angiotensin II. The inhibition of said enzyme prevents the generation of angiotensin II from I and, therefore, attenuates any pressure response following an angiotensin I challenge.

The corresponding in vivo test is performed with male, normotensive rats, which are anesthetized with 100–120 mg/kg i.p. of sodium ethyl-(1-methylpropyl)-malonylthiourea. A femoral artery and saphenous vein are cannulated for direct blood pressure measurement and i.v. administration of angiotensin I and compounds of this invention. After the basal blood pressure is stabilized, pressor responses to 3 challenges of 0.33 $\mu$g/kg of angiotension I i.v. , in 5 minute intervals, are obtained. Such pressure responses are again obtained 5, 10, 15, 30 and 60 minutes after either i.v. or p.o. administration (stomach tube) of the compounds to be tested, and compared with the initial responses. Any observed decrease of said pressor response is an indication of angiotensin I converting enzyme inhibition, ranging up to 80% or greater after 10 mg/kg i.v., or lower doses, which decrease may be sustained up to 60 minutes.

Illustrative of the invention, the representative test compound 1-(N-benzyloxycarbonyl-$\gamma$-R-glutamyl)-indoline-2S-carboxylic acid inhibits the pressor response following angiotensin I challenge by about 70% at an intravenous dose as low as 0.1 mg/kg.

The in vitro inhibition ot the angiotensin-converting enzyme by the compounds of the formula I of this invention can be demonstrated analogous to Biochim. Biophys. Acta 293, 451 (1973). According to this method, said compounds are dissolved at about 1 mM concentrations in phosphate buffer, externally cooled with ice. To these solutions various $\mu$l of histidyl-leucine in phosphate buffer are added, followed by 100 $\mu$l of 5 mM hippuryl-histidyl-leucine in phosphate buffer and 50 $\mu$l of the angiotensin-converting enzyme isolated from lungs of adult male rabbits, which is freshly prepared in Tris buffer containing potassium and magnesium chloride, as well as sucrose. Said solutions are incubated at 37° for 30 minutes and combined with 0.75 ml of 0.6 N aqueous sodium hydroxide to stop further reaction. Then 100 $\mu$l of o-phthalaldehyde are added at room temperature, and 10 minutes later 100 $\mu$l of 6N hydrochloric acid are also added. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against drug concentration to determine the IC$_{50}$, i.e., the drug concentration which gives half the activity of the control sample containing no drug. Again, said representative members of the compounds of this invention are very effective in this in vitro test system. Illustrative of the invention, the representative test compound 1-(N-benzyloxycarbonyl-$\gamma$-R-glutamyl)-indoline-2S-carboxylic acid shows an IC$_{50}$ of about 7 nM ($7 \times 10^{-9}$M).

Accordingly, the compounds of this invention are valuable antihypertensive agents, especially useful for ameliorating hypertension (regardless of etiology) and/or heart conditions, such as congestive heart failure, and/or other edemic or ascitic diseases, e.g. hepatic cirrhosis. They are also useful intermediates in the preparation of other valuable products, especially of corresponding pharmaceutical compositions containing an effective amount of the active compound.

The present invention also relates to pharmaceutical e.g., cardiovascular compositions that contain an effective amount of a compound of the formula I or a pharmaceutically acceptable salt of such compounds having a salt forming group. The pharmaceutical compositions according to the invention are suitable for enteral administration, such as oral or rectal administration, and for parenteral administration, and the compositions contain the pharmacologically active compound exclusively or together with a pharmaceutically acceptable carrier.

The new pharmaceutical compositions contain from approximately 10% to approximately 95%, preferably from approximately 20% to approximately 90% of the active compound. Pharmaceutical compositions according to the invention in dosage unit form are, for example, dragees, tablets, capsules, suppositories or ampoules. The present invention also relates to the preparation of pharmaceutical compositions which are prepared in a manner known per se, for example by means of conventional mixing, granulating, drageemaking, dissolving or lyophilizing processes.

Thus, pharmaceutical compositions for oral use may be obtained by combining the active compound with solid carriers and, optionally, adjuncts, optionally granulating a resulting mixture and processing the mixture or granulate, if desired or necessary after the addition of suitable adjuncts, to form tablets or dragee cores.

Suitable carriers are especially fillers, such as various sugars, for example lactose, saccharose, mannitol or sorbitol, cellulose preparations and/or calcium phosphates, for example tri-calcium phosphate or calcium hydrogen phosphate; also binders, such as starch pastes prepared, for example, by using maize, wheat, rice, or potato starches, gelatin, tragacanth, methylcellulose, hydroxypropylmethylcellulose, sodium carboxymethylcellulose and/or polyvinylpyrrolidone; and, if desired, disintegrators, such as the above-mentioned starches; furthermore, carboxymethyl starches,transversely cross-linked polyvinylpyrrolidone, agar, alginic acid or a salt thereof, such as sodium alginate. Adjuncts are especially flow regulators and lubricants, for example silica, talc, stearic acid or salts thereof, such as magnesium or calcium stearate, and/or polyethylene glycol. Dragee cores are provided with suitable coatings that may be resistant to gastric juice, for which there are used, inter alia, concentrated sugar solutions that optionally contain gum arabic, talc, polyvinylpyrrolidone, polyethylene glycol and/or titanium dioxide, lacquer solutions in suitable organic solvents or solvent mixtures, or, for the preparation of coatings resistant to gastric juice, solutions of suitable cellulose preparations, such as acetylcellulose phthalate or hydroxypropylmethyl-cellulose phthalate. Colorants of pigments may be added to the tablets or dragee coatings, for example to identify or characterize different doses of the active compound.

Other pharmaceutical compositions that may be administered orally are dry-filled capsules made of gelatin, and also soft, sealed capsules consisting of gelatin and plasticizer, such as glycerin or sorbitol. The dry-filled capsules may contain the active compound in the form of a granulate, for example in admixture with fillers, such as lactose, binders, such as starches, and/or lubricants, such as lactose, binders, such as starches, an/or lubricants, such as talc or magnesium stearate, and optionally stabilizers. In soft capsules, the active compound is preferably dissolved or suspended in suitable liquids, such as fatty oils, paraffin oil or liquid polyethylene glycols, and stabilizers may likewise be added.

Pharmaceutical compositions for rectal administration are, for example, in the form of suppositories consisting of a combination of the active compound and a suppository base substance. Suitable base substances for suppositories are, for example, natural or synthetic triglycerides,paraffin hydrocarbons, polyethylene glycols and higher alkanols. It is also possible to use gelatin rectal capsules that contain a combination of the active compound and a base substance. Suitable base substances are, for example, liquid triglycerides, polyethylene glycols and paraffin hydrocarbons.

For parenteral administration, aqueous solutions of the active compound in water-soluble form, for example in the form of a water-soluble salt, are especially suitable; also suitable are suspensions of the active compound such as corresponding oily injection suspensions, for which suitable lipophilic solvents or vehicles, such as fatty oils, for example sesame oil, or synthetic fatty acid esters, for example ethyl oleate or triglycerides, are used; or aqueous injection suspensions that contain substances increasing viscosity, for example sodium carboxymethylcellulose, sorbitol and/or dextran and, optionally, stabilizers.

The present invention additonally relates to the compounds of the formula I for use as medicaments, especially as antihypertensive and cardioactive agents, for example for the treatment of hypertension or congestive heart failure.

The invention likewise relates to a method of treatment of cardiovascular disease, especially hypertension or congestive heart failure, by using the compounds of the formula I or pharmaceutically acceptable, non-toxic salts of such compounds having salt forming groups as pharmacologically active substances, especially as antihypertensive agents, preferably in the form of pharmaceutical compositions. The dosage of active compound administered is dependent on the species of warm-blooded animal, the body weight, age and individual condition, and on the form of administration. The daily dose administered to a warm-blooded animal including man of about 70 kg body weight, is, on average, from approximately 25 to approximately 400 mg of the active compound.

The compounds of formula I and salts of such compounds having salt forming groups are manufactured, for example, as follows:

(a) A compound of the formula:

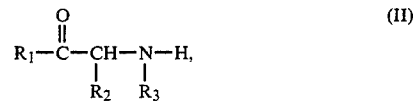

wherein $R_1$, $R_2$, and $R_3$ are defined as above is acylated by reaction with an acylating agent that introduces the acyl group of a carboxylic acid of the formula

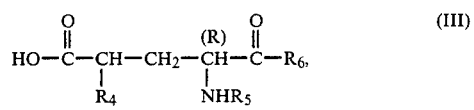

wherein $R_4$, $R_5$ and $R_6$ are defined as above, or (b) a compound of the formula:

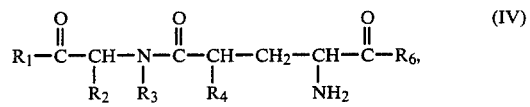

wherein $R_1$, $R_2$, $R_3$, $R_4$ and $R_6$ are defined as above, and the amino group is optionally protected by a group allowing the acylation reaction, the amino group is acylated by reaction with an acylating agent that introduces the acyl group $R_5$ and converting a protected functional group in a resulting compound prepared according to the above processes (a) and (b) into the free functional group; and/or,if desired, converting a salt into the free compound, and/or converting a resulting compound having a salt-forming group into a salt, and/or separating a resulting mixture of isomeric compounds into the separate isomers; and/or converting a resulting compound prepared according to the above processes (a) and (b) into another compound of this invention.

Process (a) (Acylation)

In a starting material of the formula II, a functional group, for example the carboxy group if $R_1$ represents hydroxy, is protected by a protecting group which is customarily used in peptide chemistry. These protecting groups should protect the functional groups from undesired side reactions, such as acylation, etherification, esterification, oxidation, solvolysis etc. and should be readily removed under mild reaction conditions, for example by cleavage, for example solvolytic, reductive, photolytic or enzymatic cleavage.

The protection of functional groups by such protecting groups, the protecting groups themselves, and reactions for their removal, are described, for example, in standard text books, such as "Protective Groups in Organic Chemistry", Plenum Press, London and New York 1973, Greene, Th. W., "Protective Groups in Organic Synthesis", Wiley, New York 1981, "The Peptides", Vol. I, Schröder and Lubke, Academic Press, London and New York 1965, and "Methoden der Organischen Chemie", Houben-Weyl, 4th Edition, Vol. 15/I, Georg Thieme Verlag, Stuttgart 1974.

A carboxy group, for example the carboxy group if $R_1$ represents hydroxy, is customarily protected in esterified form, the ester group being selectively removable under mild conditions. A carboxy group protected in esterified form is esterified especially by a lower alkyl group that is branched in the 1-position or is substituted in the 1-or 2-position of that alkyl group by suitable substituents.

A protected carboxy group esterified by a lower alkyl group that is branched in the 1-position is, for example, tert-lower alkoxycarbonyl, for example tert-butoxycarbonyl, arylmethoxycarbonyl having one or two aryl radicals wherein aryl preferably represents phenyl that is unsubstituted or mono-, di- or tri-substitued, for example by lower alkyl, for example tert-lower alkyl, for example tert-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di-(4-methoxyphenyl)-methoxycarbonyl.

A protected carboxy group esterified by a lower alkyl group that is substituted in the 1- or 2-position by suitable substituents is, for example, 1-lower alkoxy-lower alkoxycarbonyl, for example methoxymethoxycarbonyl, 1-methoxyethoxycarbonyl or 1-ethoxymethoxycarbonyl, 1-lower alkylthio-lower alkoxycarbonyl, for example 1-methylthiomethoxycarbonyl or 1-ethylthioethoxycarbonyl, aroylmethoxycarbonyl, for example phenacyloxycarbonyl, and 2-halo-lower alkoxycarbonyl, for example 2,2,2-trichloroethoxycarbonyl, 2-bromoethoxycarbonyl or 2-iodoethoxycarbonyl.

A carboxy group can also be protected in the form of an organic silyloxycarbonyl group. An organic silyloxycarbonyl group is, for example, tri-lower alkylsilyloxycarbonyl, for example trimethylsilyloxycarbonyl. The silicon atom of the silyloxycarbonyl group can instead be substituted by two lower alkyl groups, for example methyl groups, and the carboxy group or amino group of a second molecule of the formula I. Compounds having such protecting groups can be manufactured, for example, using dimethyldichlorosilane as silylating agent.

A protected carboxy group is preferably tert-lower alkoxycarbonyl, for example tert-butoxycarbonyl, benzyloxycarbonyl, 4-nitrobenzyloxycarbonyl or diphenylmethoxycarbonyl.

An acylating agent that introduces the acyl radical of a carboxylic acid of the formula III is the carboxylic acid of the formula III itself in the presence of a condensation agent, or a reactive functional derivative of this carboxylic acid.

A reactive functional derivative of this carboxylic acid of the formula III is an activated ester, a reactive anhydride or a cyclic amide of this compound.

An activated ester is especially an ester which is unsaturated at the carbon atom bonded to the carboxy group, for example a vinyl ester (obtainable by esterification of a different ester with vinyl acetate), a carbamoylvinylester (obtainable for example by treating the corresponding acid with a reagent having an isoxazolium group; 1,2-oxazolium- or Woodward method), a 1-lower alkoxyvinylester (obtainable for example by treating the corresponding acid with a lower alkoxyacetylene compound; ethoxyacetylene method), an ester of the amidino type, for example a N,N'-disubstituted amidinoester (obtainable for example by treating the corresponding free acid with a suitable N,N'-disubstituted carbodiimide, for example N,N'-dicyclohexylcarbodiimide; carbodiimide method), a N,N-disubstituted amidinoester (obtainable for example by treating the corresponding acid with a N,N-disubstituted cyanamide; cyanamide method), a suitable arylester, especially a phenylester, wherein the phenyl group is substituted by electron withdrawing groups (obtainable for example by reacting the corresponding free acid with a suitably substituted phenol compound, for example 4-nitrophenol, 4-methylsulfonylphenol, 2,4,5-trichlorophenol, pentachlorophenol, or 4-phenyldiazophenol, in the presence of a suitable condensing agent, for example N,N'-dicyclohexylcarbodiimide; activated arylester method), cyanomethylester (obtainable for example by reacting the corresponding free acid with chloroacetonitrile in the presence of a base; cyanomethylester method), a thioester, especially a phenylthioester wherein the phenyl group is optionally substituted by nitro (obtainable for example by reacting the corresponding free acid with a thiophenol which is optionally substituted by nitro; activated thioester method), or, especially, an amino- or amidoester (obtainable for example by treating the corresponding free acid with a N-hydroxyamino compound or with a N-hydroxyamido compound, respectively, for example with N-hydroxysuccinimide, N-hydroxypiperidine, N-hydroxyphthalimide, N-hydroxy-5-norbornen-2,3-dicarboxylic acid imide, or with 1-hydroxybenztriazol, for example by using the anhydride or carbodiimide method; method of the activated N-hydroxyester).

A reactive anhydride of a carboxylic acid of the formula III is, for example, a mixed anhydride of the carboxylic acid, for example a mixed anhydride with an inorganic acid, for example an acid halide, especially an acid chloride (obtainable for example by treating the corresponding free acid with a halogenating, especially a chlorinating agent, for example with thionyl chloride, phosphorous pentachloride or oxalyl chloride; acid chloride method), an azide (obtainable for example by converting a corresponding ester of the acid into the hydrazide and treating the hydrazide with nitrous acid, acid azide method), an anhydride with a carbonic acid hemiester, for example a carbonic acid lower alkyl hemiester (obtainable for example by treating the corresponding free acid with a halogenoformic acid lower alkylester, for example chloroformic acid isobutyl- or -n-butyl ester, or with a 1-lower alkoxycarbonyl-2-lower alkoxy-1,2-dihydroquinoline, for example 1-methoxycarbonyl- 2-ethoxy-1,2-dihydroquinoline, method of the mixed alkylcarbonic acid anhydride), an anhydride with a dihalogenated, especially a dichlorinated phosphoric acid (obtainable for example by treating the free acid with phosphorus oxychloride; phosphorus oxychloride method), an anhydride with other phosphorus acid derivatives (obtainable for example by reacting free acid with phenyl-N-phenylphosphoramidochloridate), an anhydride with a carboxylic acid (obtainable for example by reacting the corresponding the free acid with phenylacetic acid-, pivalic acid-, or trifluoroacetic acid chloride; method of the mixed carboxylic acid chloride anhydride, with a sulfonic acid (obtainable for example by a salt of the acid, for example the sodium salt, with a sulfonic acid halide, for example mesylchloride or p-toluenesulfonic acid; method of the mixed sulfonic acid anhydrides), a symmetric anhydride (obtainable for example by condensing the corresponding free acid in the presence of a condensation agent, for example N,N'-dicyclohexylcarbodiimide, symmetric anhydride method), or preferably a cyclic anhydride formed by the dicarboxylic acid of the formula III wherein $R_6$ is hydroxy.

A cyclic amide of a carboxylic acid of the formula III is especially a five membered diazacyclic compound of aromatic character, for example the imidazol amide (obtainable for example by reacting the corresponding free acid with carbonyldiimidazole; imidazole method), or the pyrazolone amide (obtainable for example by reacting the acid hydrazide with acetylacetone; pyrazolide method).

The condensation reaction for the preparation of compounds of the formula I can be performed in a manner which is known per se, for example by applying the solid phase method, for example by using chloromethylated resins with granulates having a diameter of 20 to 70 microns. The preparation of the resins and the acylation reaction of a carboxy and an amino compound is described in the European Pat. Application No. 81,783.

The acylation is preferably carried out in an inert, preferably anhydrous, solvent or solvent mixture, for example in a carboxylic acid amide, for example dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in mixtures thereof, optionally in the presence of an alcohol, for example methanol or ethanol, or water, optionally at reduced or elevated temperature, for example in a temperature range from approximately $-40°$ C. to approximately $+100°$ C., preferably from approximately $-10°$ C. to approximately $+50°$ C., and optionally under an inert gas atmosphere, for example nitrogen atmosphere.

Process (b) (Acylation of the amino group):

In a starting material of the formula IV, a functional group, for example the carboxy group(s) if $R_1$ and/or $R_6$ represent hydroxy, is(are) protected by a protecting group mentioned above which is customarily used in peptide- or beta-lactam chemistry.

A group allowing the acylation reaction is, for example, an organic silyl group, and also an ylidene group which, together with the amino group, forms a Schiff's base. An organic silyl group is, for example, such a group that is also capable of forming a protected carboxy group with a carboxy group $R_1$ or $R_6$, especially tri-lower alkylsilyl, especially trimethylsilyl. An ylidene group is especially a 1-aryl-lower alkylidene group, especially a 1-arylmethylene group, wherein aryl represents especially a carbocyclic, primarily a monocyclic, aryl radical, for example phenyl optionally substituted by lower alkyl, hydroxy, lower alkoxy and/or by nitro.

An acylating agent that introduces the acyl radical $R_5$ is the acid $R_5$—OH in the presence of a condensation agent or a reactive functional derivative of the acid $R_5$—OH.

A reactive, functional derivative of the acid $R_5$—OH is an activated ester, a reactive anhydride or a cyclic amide of this acid. The activated esters, reactive anhydrides or cyclic amides of the acid $R_5$—OH suitable for the acylation of the alpha-amino group in a compound of formula IV have been mentioned above under process (a).

If the free acid $R_5$—OH is used in the acylation, the acylation is customarily carried out in the presence of the same condensation agent as that used in the acylation of the amino group in a compound of the formula II with a free carboxylic acid of the formula III in accordance with process (a), for example in the presence of a carbodiimide, for example N,N'-dicyclohexyl carbodiimide.

In the acylation with the acid $R_5$—OH the same solvents are used and the same reaction conditions are maintained as in the acylation with a carboxylic acid of the formula III in accordance with process (a).

In the acylation with activated esters, reactive anhydrides or cyclic amides the same solvents, for example acetic acid or acetic anhydride, are used and the same reaction conditions are maintained as in the acylation with a reactive functional derivative of a carboxylic acid of the formula III in accordance with process (a).

In a resulting compound of the formula I in which one or more functional groups are protected, these protected groups, for example a protected carboxy group, may be freed selectively in a manner known per se by means of solvolysis, especially hydrolysis, alcoholysis or acidolysis, or by means of reduction, especially hydrogenolysis. When removing the protecting groups, reaction conditions that result in the cleaving of the acylamido group should be avoided. The reaction conditions to be maintained are described in the review article by Lakshmi P. U. and Ramachandran L. K., J. Sci. Ind. Res. 30 [12]680–688 (1971).

A protected carboxy group is freed in a manner known per se and, depending on the nature of the protecting groups, by various methods, but preferably by means of solvolysis or reduction.

Thus, tert-lower alkoxycarbonyl, or lower alkoxycarbonyl substituted in the 2-position by an organic silyl group or in the 1-position by lower alkoxy or lower alkylthio, or an optionally substituted diphenylmethoxycarbonyl can be converted into free carboxy, for example by treatment with a suitable acid, such as formic acid or trifluoroacetic acid, optionally with the addition of a nucleophilic compound, such as phenol, anisole or ethylene thioglycol. Suitably substituted benzyloxycarbonyl, such as 4-nitrobenzyloxycarbonyl, can be converted into free carboxy by reduction, for example by treatment with an alkali metal dithionite, for example sodium dithionite, or with a reducing metal, for example zinc, or a reducing metal salt, such as a chromium (II) salt, for example chromium (II) chloride, usually in the presence of an agent that yields hydrogen ions and that, together with the metal or metal salt, is capable of producing nascent hydrogen, such as an acid, especially a suitable carboxylic acid, such as a lower alkanecarboxylic acid optionally substituted, for example, by hydroxy, for example acetic acid, formic acid, glycolic acid, diphenylglycolic acid, lactic acid, mandelic acid, 4-chloromandelic acid or tartaric acid, or an alcohol or thiol, water preferably being added. By treatment with a reducing metal or metal salt, as described above, it is also possible to convert 2-halo-lower alkoxycarbonyl (optionally after conversion of a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl also by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid yielding the fluoride anion, such as an alkali metal fluoride, for example sodium or potassium fluoride, in the presence of a macrocyclic polyether ("Crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulphoxide or N,N-dimethylacetamide. Carboxy esterified by an organic silyl group, such as tri-lower alkylsilyl, for example trimethylsilyl, can customarily be freed by solvolysis, for example by treatment with water, an alcohol or an acid.

Salts of compounds of the formula I having salt forming groups, for example salts of those compounds wherein $R_1$ and/or $R_6$ represents hydroxy, can be manufactured in a manner known per se. Thus, salts of compounds of the formula I can be formed in accordance with the method described in the Examples or, for example, by reaction of the acidic groups with metal salts, such as alkali metal salts of suitable carboxylic acids, for example the sodium salt of α-ethylcaproic acid or sodium carbonate, or with ammonia or a suitable organic amine, preferably using stoichiometric quantities or only a small excess of the salt-forming agent.

Salts can be converted into the free compounds in customary manner; metal and ammonium salts can be converted, for example, by treatment with suitable acids for example hydrohalic acid, for example hydrogen chloride.

Mixtures of stereoisomers, especially mixtures of diastereomers, can be separated into the optically pure enantiomers in a manner known per se, for example by fractional crystallization or chromatography.

Racemic mixtures can be resolved in a manner known per se, for example after conversion into diastereomers, for example by reacting the racemic mixture with optically active acids or bases.

The conversion of a free carboxy group, for example the free carboxy group in compounds of the formula I, wherein $R_1$ and/or $R_6$ represents hydroxy, into an esterified carboxy group, especially into a carboxy group that can be cleaved under physiological conditions, may be effected according to esterification methods known per se. For example, a compound of the formula I in which the carboxy group to be esterified is in free form or a compound of the formula I in which the carboxy group to be esterified is in the form of a reactive functional derivative, or a salt of a compound of the formula I is reacted with the corresponding alcohol or with a reactive functional derivative of this alcohol.

In the esterification with the desired alcohol of a compound of the formula I in which the carboxy group to be esterified is in free form, the same condensation agents, for example carbodiimides, and the same solvents are used and the same reaction conditions are maintained as in the acylation in accordance with process (a).

A compound of the formula I in which the carboxy group to be esterified is in the form of a reactive functional derivative is, for example, a mixed anhydride or an activated ester, which can be obtained in the manner described under process (a) (acylation) by condensation of the carboxylic acid of the formula I with an inorganic acid, a carboxylic acid, a semiester of carbonic acid or with a sulphonic acid or by condensation with a vinylogous alcohol.

A reactive functional derivative of the alcohol to be esterified is especially the ester that is formed by condensation with a strong inorganic or organic acid, for example the corresponding halide, for example chloride, bromide or iodide, or the corresponding lower alkanesulphonyloxy compound, for example the methanesulphonyloxy compound.

In the esterification with the corresponding alcohol of a compound of the formula I in which the carboxy group to be esterified is in the form of a reactive functional derivative, or in the esterification with a reactive functional derivative of the corresponding alcohol of a compound of the formula I in which the carboxy group to be esterified is in the free form, the same solvents are used and the same reaction conditions are maintained as in the acylation with a reactive functional derivative of a carboxylic acid of the formula III in accordance with process (a).

A compound of the formula I in which the carboxy group to be esterified is in the form of a reactive functional derivative may also be manufactured in situ analogously to the method described under process (a) (acylation) and reacted with the corresponding alcohol without being isolated.

In a compound of formula I, wherein $R_1$ and/or $R_6$ represent amino, the terminal carboxamido group(s) can be substituted. Moreover, in a compound of the formula I, wherein $R_1$ and/or $R_6$ represent hydroxy, the terminal carboxy group(s) can be converted to the carboxamido or substituted carboxamido groups.

The substitution of the terminal carboxamido group(s) is effected, for example, by alkylation. Suitable alkylating agents are, for example, diazo compounds, for example diazomethane.

Diazomethane can be decomposed in an inert solvent and the free methylene moiety then reacts with the carboxamido group(s) in the compound of the formula I. The decomposition of diazomethane preferably is effected with a catalyst, for example in the presence of a noble metal in the form of a triturated powder, for example copper, or in the presence of a salt of a noble metal, for example copper(I)-chloride or copper(II)-sulfate.

Other suitable alkylating agents are mentioned in the German Pat. application 2,331,133 (Deutsche Offenlegungsschrift), for example alkyl halides, sulfonic acid esters, Meerwein salts, or 1-substituted 3-aryltriazenes, which can all be reacted with compounds of the formula I having terminal carboxamido group(s) under the reaction conditions mentioned in this publication.

The conversion of a compound of the formula I, wherein $R_1$ and/or $R_6$ denotes hydroxy, to a compound having terminal carboxamido group(s) can be effected by amidation with ammonia or with a primary or secondary amine. Moreover, a compound of the formula I having esterified carboxy group(s) can be converted by ammonolysis with ammonia to a compound of formula I having terminal carboxamido group(s). If the ammonolysis is performed with a primary or secondary amine, compounds of formula I having terminal substituted carboxamido group(s) are obtained.

The amidation or ammonolysis can be effected according to standard procedures, for example according to the reaction conditions mentioned for these processes in the "Organikum", latest edition, VEB Deutscher Verlag der Wissenschaften, Berlin (East).

The process also includes those embodiments according to which compounds formed as intermediates are used as starting materials and the remaining process steps are carried out with these, or the process is discontinued at any stage; furthermore, starting materials may be used in the form of derivatives or may be formed during the reaction.

Preferably, the starting materials and the reaction conditions are so chosen that the compounds described above as being especially preferred are obtained.

The starting materials of the formulae II and III used in the process according to this invention are known. Most of the compounds falling within the scope of formulae II and III are commercially available.

The starting materials of the formula IV can be prepared in manner known per se, for example by acylating a compound of formula II with a carboxylic acid of formula III wherein $R_5$ represents hydrogen, or a reactive functional derivative thereof, according to process a).

The following examples illustrate the above-described invention; however, they are not intended to restrict its scope in any way whatsoever. Temperatures are given in degrees Centigrade. Unless mentioned otherwise, the evaporation of the solvent is performed under reduced pressure, preferably between about 15 and 100 mm HG. Unless stated otherwise, optical rotations are measured in methanol at room temperature.

1.
1-(N-Benzyloxycarbonyl-γ-R-glutamyl)indoline-2-S-carboxylic acid (a) To a solution of 22.5 g of indoline-2S-carboxylic acid hydrochloride in 150 ml of pyridine under an atmosphere of nitrogen, 30 g of N-benzyloxycarbonyl-R-glutamic acid anhydride is added. The mixture is heated to 80° for 5 h and left to stir at room temperature overnight. The solvent is removed and the residue is cooled in an ice bath, diluted with 100 ml of water and acidified with 40 ml of concentrated hydrochloric acid giving a viscous residue. The residue is solidified, broken up and washed with methylene chloride. The solid obtained is collected, washed with 200 ml of water and air dried overnight. The solid is again suspended in 70 ml of chloroform, filtered, washed with chloroform, and dried at high vacuum for 4 h to yield the title compound as a colorless solid melting at 186°–188°; $[\alpha]_D = -60°$ (c=1% in ethanol).

(b) The starting material N-benzyloxycarbonyl-R-glutamic acid anhydride is prepared by heating 60 g of N-benzyloxycarbonyl-R-glutamic acid with 600 ml of acetic acid anhydride at 60° for 3 h. After concentrating and drying, the crystalline solid melting at 91°–93° is obtained.

2.
1-(N-Benzyloxycarbonyl-γ-R-glutamyl)octahydroindolyl-2S-carboxylic acid (a) To a solution of 0.5 g of perhydroindoline-2Scarboxylic acid hydrochloride in 10 ml of pyridine under an atmosphere of nitrogen, 0.64 g of N-benzyloxycarbonyl-R-glutamic acid anhydride is added. The mixture is heated to 70° for 5 h. The solvent is removed and the residue is cooled in an ice bath, acidified to pH 2 with 2N HCl and extracted with methylene chloride. After concentrating the organic extract, the residue is treated with 5% aqueous sodium bicarbonate solution, and shaken with ether. The basic aqueous layer is cooled, acidified again with 2N HCl, extracted with $CH_2Cl_2$, dried over sodium sulfate, concentrated, suspended in hexane, and filtered to yield the title compound as a colorless solid melting at 79°–82°; $[\alpha]_D = -21.0°$ (c=1.8%).

3.
1-[N-(dihydrocinnamoly)-γ-R-glutamyl]-indoline-2S-carboxylic acid (a) To a solution of 0.33 g of sodium hydroxide in 4 ml of water and 1.2 g of 1-(γ-R-glutamyl)-indoline-2S-carboxylic acid cooled to 0°, 0.16 g of sodium hydroxide in 2 ml of water and 0.69 g of dihydrocinnamoyl chloride are simultaneously added. The mixture is stirred overnight, filtered, cooled, and acidified with 2.5 ml of concentrated hydrochloric acid. The colorless solid is collected, washed with water, dried at 50° under high vacumm overnight to yield the title compound melting at 196°–198°; $[\alpha]_D = -65.9°$ (c=1%).

(b) The starting material is prepared as follows:
A solution of 18 g of 1-(N-benzyloxycarbonyl-γ-R-glutamyl)-indoline-2S-carboxylic acid in 450 ml of absolute ethanol with 3.6 g of suspended 10% palladium on charcoal is hydrogenated at atmospheric pressure. The product crystallizes out of solution and is removed by filtration. The crude product is separated from the catalyst by treating the mixture with 400 ml of hot water, filtering, and washing with another 100 ml aliquot of hot water. The aqueous filtrate is concentrated to about 250 ml and cooled in an ice bath. The precipitate is collected and dried to yield the 1-(γ-R-glutamyl)-indoline-2S-carboxylic acid melting at 193°–195°; $[\alpha]_D = -110°$ (c=1% in ethanol).

4. 1-(N-Benzoyl-1-R-glutamyl)-indoline-2-S-carboxylic acid

To a solution of 1.2 g of 1-(γ-R-glutamyl)-indoline-2S-carboxylic acid and 0.33 g of sodium hydroxide in 4 ml of water cooled in an ice bath, 0.57 g of benzoyl chloride and 0.16 g of sodium hydroxide in 2 ml of water are added. The reaction mixture is stirred at room temperture overnight, filtered, washed with ether cooled to 0°–5°, and acidified with 1.5 ml of concentrated hydrochloric acid. The oil slowly solidifies and the solid is collected, washed with water and dried at 80° for 4 hours to yield the title compound melting at 120°–123°; $[\alpha]_D = -70.2°$ (c=1%).

5.
1-(N-Nicotinoyl-γ-R-glutamyl)-indoline-2S-carboxylic acid

To a solution of 1.05 g of nicotinic acid and 1.6 g of N-hydroxy-5-norbornene-2,3-dicarboximide in 30 ml of dimethylformamide, 1.94 g of N,N-dicyclohexylcarbodiimide is added. The mixture is stirred for 3.5 hours at room temperature, filtered, and 2.50 g of 1-(γ-R-glutamyl)-indoline-2S-carboxylic acid is added to the filtrate. The mixture is heated to 70° overnight, concentrated, and triturated with 20 ml of water. The solid is collected, washed with cold water and dried. The solid is partitioned between 100 ml of hot ethyl acetate and 25 ml of hot water. The aqueous layer is allowed to stand overnight and the crystalline title compound is collected and dried at 100° overnight. The product melts at 178°-180°; $[\alpha]_D = -63.6°$ (c=0.5%).

6.
1-(N-Phenylcarbamoyl-γ-R-glutamyl)-indoline-2S-oarboxylic aold

To a suspension of 1.0 g of 1-(γ-R-glutamyl)-indoline-2S-carboxylic acid in 20 ml of dimethylformamide 0.407 g of phenylisocyanate is added. The mixture is stirred for 2 days at room temperature. A small amount of insoluble material is removed by filtration. The filtrate is concentrated and partitioned between ethyl ether and 15 ml of 5% aqueous sodium carbonate. The basic aqueous layer is separated, washed with ether, cooled, and acidified with 3 ml of concentrated hydrochloric acid. The solid is collected, washed with water, stirred vigorously in ether, filtered and dried under high vacuum to yield the title compound melting at 158°-161°; $[\alpha]_D = -88.4°$ (c=0.25%).

7.
1-(N-p-Toluenesulfonyl-γ-R-glutamyl)-indoline-2S-carboxylic acid

To a solution of 1.2 g of 1-(γ-R-glutamyl)-indoline-2S-carboxylic acid and 0.49 g of sodium hydroxide in 5 ml of water cooled in an ice bath 0.78 g of p-toluenesulfonylchloride is added. The mixture is stirred at room temperature overnight, cooled in an ice bath, acidified with 1 ml of concentrated hydrochloric acid and extracted three times with ethyl acetate. The organic extracts are dried over sodium sulfate, filtered, and concentrated to give a foam which solidifies after stirring with 25 ml of ether. The solid is collected and dried under high vacuum to yield the title compound melting at 138°-140°; $[\alpha]_D = -90°$ (c=0.25%).

8.
1-(N-p-Benzenesulfonyl-γ-R-glutamyl)-indoline-2S-carboxylic acid

In a manner analogous to Example 7, the title compound melting at 168°-170, $[\alpha]_D = -65°$ (c=1%), can be prepared.

9.
1-(N-Picolinoyl-γ-R-glutamyl)-indoline-2S-carboxcylic acid (a) A solution of 1.0 g of 1-(γ-R-glutamyl)-indoline-2S-carboxylic acid and 0.75 g of N-picolinoyloxysuccinimide in 15 ml of dimethylformamide is heated to 80° for 2 h and then stirred at room temperature overnight. The mixture is concentrated and stirred with 40 ml of water which initiates crystallization. The solid is collected and dried to yield the title compound melting at 159°-161°; $[\alpha]_D = -77°$ (c=0.25%).

(b) Preparation of the starting material:
The N-picolinoyloxysuccinimide is prepared by adding 8.4 g of N,N'-dicyclohexylcarbodiimide to a solution of 5.0 g of picolinic acid and 4.7 g of N-hydroxysuccinimide in 50 ml of dimethylformamide. The mixture is stirred overnight, triturated with ether and recrystallized from ethyl acetate, methylene chloride (1:1). The solid is collected and dried; mp. 174°-175°.

10. 1-(N-Acetyl-γ-R-glutamyl)-indoline-2S-carboxylic acid

To a solution of 3.5 ml of acetic anhydride, 7 ml of acetic acid and 10 ml of water 0.70 g of 1-(γ-R-glutamyl)-indoline-2S-carboxylic acid is added. The mixture is stirred for 15 h and concentrated under reduced pressure. The resulting solid is dissolved in 10 ml of methanol and triturated with water. The colorless solid is collected to yield the title compound melting at 200°-202°; $[\alpha]_D = -110°$ (c=0.25%).

11.
1-(N-Benzyloxycarbonyl-γ-R-ethoxyglutamoyl)-indoline-2S-carboxylic acid (a) To a solution of 1.3 g 1-(N-Benzyloxycarbonyl-γ-R-ethoxyglutamoyl)-indoline-2S-carboxylic acid ethyl ester in 200 ml absolute ethanol 2.69 ml of 1 N lithium hydroxide solution is added. The solution is stirred overnight at room temperature, filtered to remove residual solids, and concentrated to dryness. The residue is partitioned between ether and water. The aqueous layer is separated and washed twice with ether, cooled in an ice bath, and acidified with concentrated hydrochloric acid. The resulting oil is extracted with methylene chloride, dried over $Na_2SO_4$, filtered and concentrated to give a foam. The foam is flash chromatographed on silica gel eluting with ethyl acetate-methanol (9:1) to yield the title compound melting at 68°-71°; $[\alpha]_D = -46°$ (c=0.9%).

Preparation of the starting material:

(b) 1-(N-Benzyloxycarbonyl-γ-R-ethoxyglutamoyl)-indoline-2S-carboxylic acid ethyl ester is prepared by refluxing 2.0 g of 1-(N-benzyloxycarbonyl-γ-R-ethoxyglutamoyl)-indoline-2S-carboxylic acid and 0.4 ml of concentrated sulfuric acid in 80 ml of ethanol for 4 h. The mixture is concentrated, dissolved in 80 ml of ether, washed with 5% sodium bicarbonate solution, water, dried over $Na_2SO_4$, filtered, and concentrated. The residue is crystallized from hot ethanol to yield the diester melting at 117°-120°; $[\alpha]_D = -55.3°$ (c=0.9%).

12.
1-(N-Nicotinoyl-γ-R-ethoxyglutamoyl)-indoline-2S-carboxylic acid a) To an ice-cold solution of 1.0 g of ethyl N-nicotinoyl-o-R-glutamate in 20 ml of methylene chloride 0.60 g of 1,1'-carbonyldiimidazole in 10 ml of methylene chloride is added. The mixture is stirred for 1.5 h and 0.71 g of indoline-2S-carboxylic acid in 8 ml of pyridine is added. The reaction mixture is stirred an additional 15 h at room temperature and concentrated to give a gummy residue. The residue is treated with 20 ml of 5% aqueous sodium bicarbonate solution and extracted twice with ether. The basic aqueous phase is cooled in an ice bath and the pH-value of the solution is adjusted to 4.0. The precipitate is collected and washed with water, dried under high vacuum yielding the title compond which melts at 231°-233°; $[\alpha]_D = -40°$ (c=0.5%).

Preparation of the starting material:

(b) Ethyl N-nicotinoyl-α-R-glutamate is prepared by heating 1.0 g of α-ethyl-R-glutamate $[\alpha]_D = -14.2°$ (c=1%), and 1.25 g of N-nicotinoylsuccinimide (prepared as described in example (9b) by substituting nicotinic acid for picolinic acid) in 20 ml of dimethylformamide for 2 h at 80°. The mixture is concentrated and 10 ml of water is added. The colorless solid is collected, washed with cold water and dried under high vacuum to give the acid-ester melting at 157°–159°; $[\alpha]_D = +18.4°$ (c=1%).

13. 1-(N-Benzyloxycarbonyl-γ-R-glutamyl)-indoline-2-S-carboxylic acid-3-pyridylmethyl ester (a) A solution of 1.25 g of N-benzyloxycarbonyl-R-glutamic acid anhydride and 1.2 g of indoline-2S-carboxylic acid-3-pyridylmethylester in 10 ml of tetrahydrofuran is refluxed for 18 h. The mixture is concentrated and recrystallized from 20 ml of ethyl acetate:ethanol (3:1). The colorless solid is collected, rinsed with cold ethyl acetate and dried under high vacuum to give the title compound melting at 157°–158°; $[\alpha]_D = -63°$ (c=0.5%).

Preparation of the starting material:

(b) Indoline-2S-carboxylic acid-3-pyridylmethylester is prepared by azeotropic removal of water from the mixture of 3-pyridylcarbinol, indoline-2S-carboxylic acid and p-toluene sulfonic acid in toluene using a Dean-stark trap.

14.
1-(N-Benzyloxycarbonyl-γ-R-glutamyl)-indoline-2S-carboxylic acid-3-dimethylaminopropylester (a) To a solution of 1.0 g of indoline-2S-carboxylic acid-3-dimethylaminopropyl ester in 10 ml of methylene chloride is added 1.06 g of N-benzyloxycarbonyl glutamic acid anhydride. The mixture is stirred at room temperature for 15 h, concentrated and recrystallized from ethanol yielding the title compound which melts at 167°–169°; $[\alpha]_D = -34.5°$ (c=0.25%).

Preparation of the starting material:

(b) Indoline-2S-carboxylic acid-3-dimethylaminopropyl ester is prepared by azeotropic removal of water from the mixture of 3-dimethylamino-1-propanol, indoline-2S-carboxylic acid and p-toluene sulfonic acid in toluene using a Dean-Stark trap.

15.
1-(N-Benzyloxycarbonyl-γ-R-glutamyl)-indoline-2S-carboxylic acid-2-dimethylaminoethylester Analogous to the method described in Example 14 the title compound which melts at 178°–179°, $[\alpha]_D = -52°$ (c=1%), can be prepared.

16.
1-(N-Benzyloxycarbonyl-γ-R-glutamyl)-indoline-2S-carboxylic acid ethylester

To a solution of 1.14 g of indoline-2S-carboxylic acid ethylester hydrochloride in 15 ml of pyridine 1.31 g of N-carbobenzoxy-R-glutamic acid anhydride is added. The mixture is heated to 80° for 5 hours, stirred at room temperature overnight, concentrated, and partitioned between 20 ml of ether and 40 ml of 5% sodium bicarbonate. The basic aqueous layer is separated, washed with ether, cooled in an ice bath, and acidified with 5 ml of concentrated hydrochloric acid. After extraction with methylene chloride, the organic phase is dried over Na₂SO₄, filtered and concentrated to give a foam. The crude product is purified by flash chromatography on silica gel eluting with ethyl acetate yielding the title compound which melts at 74°–77°; $[\alpha]_D = -59.4°$ (c=1%).

17.
1-(N-Benzyloxycarbonyl-γ-R-glutamyl)-indoline-2S-carboxamide (a) To a solution of 0.50 g of indoline-2S-carboxamide in 30 ml of pyridine is added at 80° 0.81 g of N-benzyloxycarbonyl-R-glutamic acid anhydride. The mixture is heated at 80° for 15 h. The solvent is removed and the residue is acidified with 15 ml of 2N hydrochloric acid. The solid is collected and recrystallized from ethyl acetate, ethanol (4:1) yielding the title compound melting at 190°–192°; $[\alpha]_D = -85.6°$ (c=1%).

Preparation of the starting material:

The indoline-2S-carboxamide is prepared by stirring for 48 h, 2.0 g of indoline-2S-carboxylic acid ethylester in 20 ml of methanol that is previously saturated with ammonia. The solid is collected, washed with methanol, water, and dried to give the amide melting at 225°–227°.

18.
1-[2-R-Methyl-4-N-benzyloxycarbonyl-4-carboxy-4-R-butyryl]-indoline-2-S-carboxylic acid (a) To a solution of 1 mM of 1-[2-R-methyl-4-N-benzyloxycarbonylamino-4-ethoxycarbonyl-4-R-butyryl]-indoline-2-S-carboxylic acid ethylester in 2 ml of methanol 2 ml of 1 N sodium hydroxide solution is added. The solution is stirred 1 h at room temperature, cooled in an ice bath and 2 ml of 1 N hydrochloric acid is added. The mixture is extracted separately with ethyl acetate and methylene chloride. The organic layers are combined, dried over Na₂SO₄, filtered and concentrated to give the title compound.

Preparation of the starting material:

(b) To a solution of 2.2 g of indoline-2-S-carboxylic acid hydrochloride in 15 ml of pyridine 3.2 g of 2-benzyloxycarbonylamino-4-methyl-pentandioic acid anhydride is added. The mixture is heated to 80° for 5 h and left to stir at room temperature overnight. The mixture is concentrated, diluted with 100 ml of water, cooled, and acidified with 4 ml of concentrated hydrochloric acid. The mixture is extracted with ethyl acetate and methylene chloride. The organic layers are combined, dried over Na₂SO₄ and concentrated. The residue is dissolved in 30 ml of ethanol containing two drops of concentrated sulfuric acid and refluxed 3 hours. The mixture is concentrated, ethyl acetate added and washed with 5% sodium bicarbonate, dried concentrated, and chromatographed on silica gel to give 1-[2-R-methyl-4-N-benzyloxycarbonylamino-4-ethoxycarbonyl-4-R-butyryl]indoline-2-S-carboxylic acid ethylester.

19.
1-[2-R-Methyl-4-N-benzyloxycarbonylamino-4-ethoxycarbonyl-4-R-butyryl]-indoline-2-S-carboxylic acid To a solution of 1 m Mol of 1-[2-R-methyl-4-N-benzyloxycarbonyl-4-ethoxycarbonyl-4-R-butyryl]-indoline-2-S-carboxylic acid ethylester in 20 ml of absolute ethanol 1 ml of 1 N lithium hydroxide solution is added. The solution is stirred overnight at room temperature, filtered to remove residual solids, and concentrated to dryness. The residue is partitioned between ether and water. The aqueous layer is separated and washed twice with ether, cooled in an ice bath, and acidified with concentrated hydrochloric acid. The residue is extracted with methylene chloride, dried over Na₂SO₄, concentrated and chromatographed on silica gel to give the title compound.

20. The following compounds are prepared in a manner analogous to the preceeding Examples:

(a) 1-(N-benzyloxycarbonyl-γ-R-glutamyl)-decahydroisoquinoline-3-S-carboxylic acid, m.p. 61°–64°, $[\alpha]_D = +7.8°$ (1.9%);

(b) 1-(N-benzyloxycarbonyl-γ-R-glutamyl)-1,2,3,4-tetrahydroisoquinoline-3-S-carboxylic acid, m.p. 87°–89°, $[\alpha] = 14.0°$ (1.5%);

(c) I-(N-benzyloxycarbonyl-γ-R-glutamyl)-1,2,3,4-tetrahydroisoquinoline-3-S-oarboxylic acid, m.p. 87°–89°, $[\alpha]_D = 14.0°$ (c=1.5%);

(d) I-(N-benzyloxycarbonyl-γ-R-glutamyl)-1,2,3,4-tetrahydroisoquinoline-2-carboxylic acid, m.p. 77°–80°;

(e) N-benzyloxycarbonyl-γ-R-glutamyl)-N-3,4-dimethoxyphenylaminoacetic acid, m.p. 75°–79°, $[\alpha]_D = +0.5°$ (1%);

(f) 1-(N-benzyloxycarbonyl-γ-glutamyl)-S-proline, m.p. 53°–55°, $[\alpha]_D = 33.2°$ (0.5%);

(g) (N-benzyloxycarbonyl-γ-glutamyl)-N-cyclopentyl-aminoacetic acid, m.p. 75°–79°, $[\alpha]_D = +8.0°$ (1%);

(h) 1-(N-benzyloxycarbonyl-γ-glutamyl)-2-(2-hydroxyphenyl)-5-carboxythiazoline, m.p. 108°–110°, $[\alpha]_D = 11.2°$ (1%).

21. Preparation of 10,000 tablets each containing 10 mg of the active compound of Example 1:

| Composition: | |
|---|---|
| 1-(N—Benzyloxycarbonyl-γ-R-glutamyl)indoline-2-S—carboxylic acid | 100.00 g |
| Lactose | 1,157.00 g |
| Corn Starch | 75.00 g |
| Polyethylene glycol 6,000 | 75.00 g |
| Talcum powder | 5.00 g |
| Magnesium stearate | q.s. |

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

22. Preparation of 10,000 capsules each containing 10 mg of the active ingredient of Example 1:

| Composition: | |
|---|---|
| 1-(N—Benxyloxycarbonyl-γ-R-glutamyl)indoline-2-S—carboxylic acid | 100.00 g |
| Lactose | 1,800.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

Analogously, tablets or capsules are prepared from the remaining compounds of the invention, e.g., those illustrated by the examples herein.

What is claimed is:

1. A compound of the formula

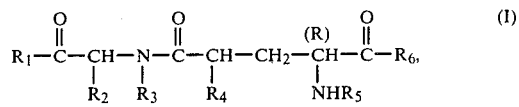

wherein $R_1$ represents hydroxy, $C_1$-$C_4$-alkoxy, di-$C_1$-$C_4$-alkylamino-$C_2$-$C_4$-alkoxy, pyrid-2-, -3-or -4-ylmethoxy, or amino; $R_2$ and $R_3$ together with the adjacent —CH— group and the adjacent N-atom form a octahydroindolyl or a dihydroindolyl moiety; $R_4$ represents hydrogen; $R_5$ is carbamoyl, $C_1$-$C_4$-alkanoyl, nicotinoyl, isonicotinoyl, picolinoyl, $C_1$-$C_4$-alkoxycarbonyl, benzyloxycarbonyl, $C_1$-$C_4$-alkylsulfonyl, benzenesulfonyl or p-toluenesulfonyl; and $R_6$ represents hydroxy, $C_1$-$C_4$-alkoxy, de-$C_1$-$C_4$-alkylamino-$C_2$-$C_4$-alkoxy, pyrid-2-, -3- or -4-ylmethoxy; or a pharmaceutically acceptable salt of a compound of the formula I that has a free carboxy group or a basic salt forming group.

2. A compound according to claim 1 wherein $R_1$ represents hydroxy, $C_1$-$C_4$-alkoxy, di-$C_1$-$C_4$-alkylamino-$C_2$-$C_4$alkoxy, pyrid-2-, -3- or -4-ylmethoxy, or amino; $R_2$ and $R_3$ together with the adjacent -CH- group an the adjacent N-atom form a octahydroindolyl or dihydroindolyl moiety; $R_4$ represents hydrogen, $R_5$ represents $C_1$-$C_4$-alkanoyl, nicotinoyl, isoicotinyl, picolinoyl, benzyloxycarbonyl, mesyl, benzenesulfonyl, or p-toluenesulfonyl; and $R_6$ represents hydroxy or $C_1$-$C_4$-alkoxy; or a pharmaceutically acceptable salt of a said compound of the formula I that haa a free carboyx group or has a basic salt forming group.

3. A compound according to claim 1 having the formula

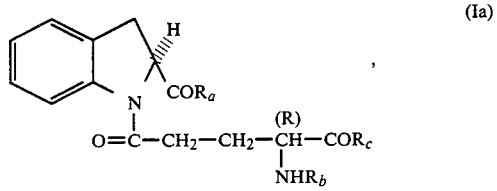

wherein $R_a$ represents hydroxy, $C_1$-$C_4$-alkoxy, di-$C_1$-$C_4$-alkyl amino-$C_2$-$C_4$-alkoxy, pyrid-2-, -3- or -4-ylmethoxy, or amino; $R_b$ represents $C_1$-$C_4$-alkanoyl, nicotinoyl, isonicotinoyl, picolinoyl, benzyloxycabonyl, $C_1$-$C_4$-alkylsulfonyl, benzenesulfonyl or p-toluenesulfonyl; and $R_c$ represents hydroxy or $C_1$-$C_4$-alkoxy; or a pharmaceutically acceptable salt of a said compound of the formula Ia that has a free carboxy group or has a basic salt forming group.

4. A compound of claim 3 and formula Ia wherein $R_a$ represents hydroxy, methoxy, ethoxy, 2-dimethylaminoethoxy, 3-dimethylamino-n-propoxy, or pyrid-2-, -3- or -4-ylmethoxy, or amino; $R_b$ represents acetyl, nicotinoyl, isoicotinyl picolinoyl, benzyloxycarbonyl, meshyl, benzenesulfonyl or p-toluenesulfonyl; and $R_c$ represents hydroxy, methoxy or ehtoxy; or a pharmaceutically acceptable salt of a compound of the formula Ia that has a free carboxy group or has a basic salt forming group.

5. A compound according to claim 2 being 1-(N-benzyloxycarbonyl-γ-R-glutamyl)-indoline-2-S-carboxylic acid or a pharmaceutically acceptable salt thereof.

6. A compound according to claim 2 being 1-(N-nicotinoyl-γ-R-glutamyl)-indoline-2-S-carboxylic acid or a pharmaceutically acceptable salt thereof.

7. A compoun- according to claim 2 being 1-(N-p-toluenesulfonyl-γ-R-glutamyl)-indoline-2-S-carboxylic acid or a pharmaceutically acceptable salt thereof.

8. An angiotensin converting enzyme inhibiting pharmaceutical composition which contains an effective angiotensin-converting enzyme inhibiting amount of a compound of claim 2 together with a pharmaceutically acceptable adjunct or carrier.

9. A method for the treatment of cardiovacular diseases responsive to angiotensin-converting enzyme inhibition in a mammal comprising administering to a mammal in need of said treatment an effective angiotensin-converting enzyme inhibiting amount of a compound of claim 2 or of a pharmaceutical composition comprising said compound together with one or more pharmaceutically acceptable carriers.

10. A method according to claim 9 for the treatment of hypertension.

11. A method according to claim 9 for the treatment of congestive heart failure.

* * * * *